(12) United States Patent
Serola

(10) Patent No.: US 8,591,445 B2
(45) Date of Patent: Nov. 26, 2013

(54) SACROILIAC BELT AND COMPOSITE STRUCTURE

(75) Inventor: Richard J. Serola, Roscoe, IL (US)

(73) Assignee: Richard J. Serola, Loves Park, IL (US)

(\*) Notice: Subject to any disclaimer, the term of this patent is extended or adjusted under 35 U.S.C. 154(b) by 0 days.

(21) Appl. No.: 11/696,286

(22) Filed: Apr. 4, 2007

(65) Prior Publication Data

US 2007/0232974 A1    Oct. 4, 2007

Related U.S. Application Data

(63) Continuation-in-part of application No. 11/278,632, filed on Apr. 4, 2006, now abandoned.

(51) Int. Cl.
*A61F 5/00* (2006.01)

(52) U.S. Cl.
USPC .................................. 602/19; 602/5

(58) Field of Classification Search
USPC ............... 602/19, 5; 482/139; 128/869, 876; 2/336–338
See application file for complete search history.

(56) References Cited

U.S. PATENT DOCUMENTS

| | | |
|---|---|---|
| 3,256,882 A | 6/1966 | Huber |
| 3,561,436 A | 2/1971 | Gaylord, Jr. |
| 3,587,570 A | 6/1971 | Kilbey |
| 3,605,731 A | 9/1971 | Tigges |
| 3,926,183 A | 12/1975 | Spiro |
| 4,097,576 A | 6/1978 | Tamura et al. |
| 4,099,524 A \* | 7/1978 | Cueman et al. ............... 602/19 |
| 4,572,167 A | 2/1986 | Brunswick |
| 4,576,154 A | 3/1986 | Hyman et al. |
| 4,628,918 A | 12/1986 | Johnson, Jr. |
| 4,685,668 A \* | 8/1987 | Newlin, Jr. .................. 482/106 |
| 4,696,291 A | 9/1987 | Tyo |
| 4,703,750 A | 11/1987 | Sebastian et al. |
| 4,715,364 A | 12/1987 | Noguchi |
| D296,930 S | 7/1988 | Carabelli |
| 4,782,535 A | 11/1988 | Yewer, Jr. et al. |
| 4,795,779 A | 1/1989 | Tazawa et al. |
| 4,836,194 A | 6/1989 | Sebastian et al. |
| 4,907,576 A \* | 3/1990 | Curlee ............................ 602/19 |
| 5,036,838 A | 8/1991 | Sherman |
| 5,086,759 A \* | 2/1992 | Buddingh ...................... 602/19 |
| 5,165,402 A | 11/1992 | McCoy |

(Continued)

FOREIGN PATENT DOCUMENTS

GB    2 094 631 A    9/1982

*Primary Examiner* — Michael A. Brown

(74) *Attorney, Agent, or Firm* — Reinhart Boerner Van Deuren P.C.

(57) ABSTRACT

A sacroiliac belt with a non-elastic inner belt to wrap around the user's hips and an elastic outer belt to wrap from the back to opposite sides of the inner belt. Non-cinchable hook and loop fastener construction is used to secure the inner and outer belts in position. The inner belt includes an inside elastomeric foam layer with open-cell frictional gripping surface, a non-elastic outside layer of loop material, and a hook tab for engaging the loop material to close the belt. The inner belt may be established with a non-elastic composite foam-fabric structure comprising a bi-laminate of the foam and elastic fabric, and a strip of loop material secured lengthwise onto the fabric side of the bi-laminate. The outer belt includes an elastic strip and hook tabs for connecting to the strip of loop material. The non-elastic composite foam-fabric may be used in other orthopedic braces and supports.

14 Claims, 7 Drawing Sheets

(56) References Cited

U.S. PATENT DOCUMENTS

| | | | |
|---|---|---|---|
| 5,188,585 A * | 2/1993 | Peters | 602/19 |
| D338,997 S | 9/1993 | Greco | |
| 5,316,022 A | 5/1994 | Schiek, Sr. | |
| 5,399,151 A | 3/1995 | Smith | |
| 5,421,809 A | 6/1995 | Rise | |
| 5,437,618 A | 8/1995 | Sikes | |
| 5,500,959 A | 3/1996 | Yewer, Jr. | |
| 5,551,085 A * | 9/1996 | Leighton | 2/44 |
| 5,586,969 A * | 12/1996 | Yewer, Jr. | 602/19 |
| 5,690,609 A | 11/1997 | Heinze, III | |
| 5,722,940 A | 3/1998 | Gaylord, Jr. et al. | |
| 5,776,087 A * | 7/1998 | Nelson et al. | 602/19 |
| 5,899,870 A | 5/1999 | Deirmendjian et al. | |
| 5,984,885 A | 11/1999 | Gaylord, Jr. et al. | |
| 6,149,617 A | 11/2000 | McNally et al. | |
| 6,506,175 B1 | 1/2003 | Goldstein | |
| 6,783,506 B2 | 8/2004 | Seering et al. | |
| 6,861,379 B1 | 3/2005 | Blaszczykiewicz | |
| 7,037,284 B2 * | 5/2006 | Lee | 602/19 |
| 7,052,638 B2 * | 5/2006 | Clarner et al. | 264/167 |
| D548,350 S | 8/2007 | Jordan et al. | |
| 8,086,579 B1 | 12/2011 | Chandrasekaran et al. | |
| 2004/0031130 A1 | 2/2004 | Clarner | |
| 2004/0193082 A1 | 9/2004 | Cofre | |
| 2006/0122547 A1 | 6/2006 | Stewart, III et al. | |

\* cited by examiner

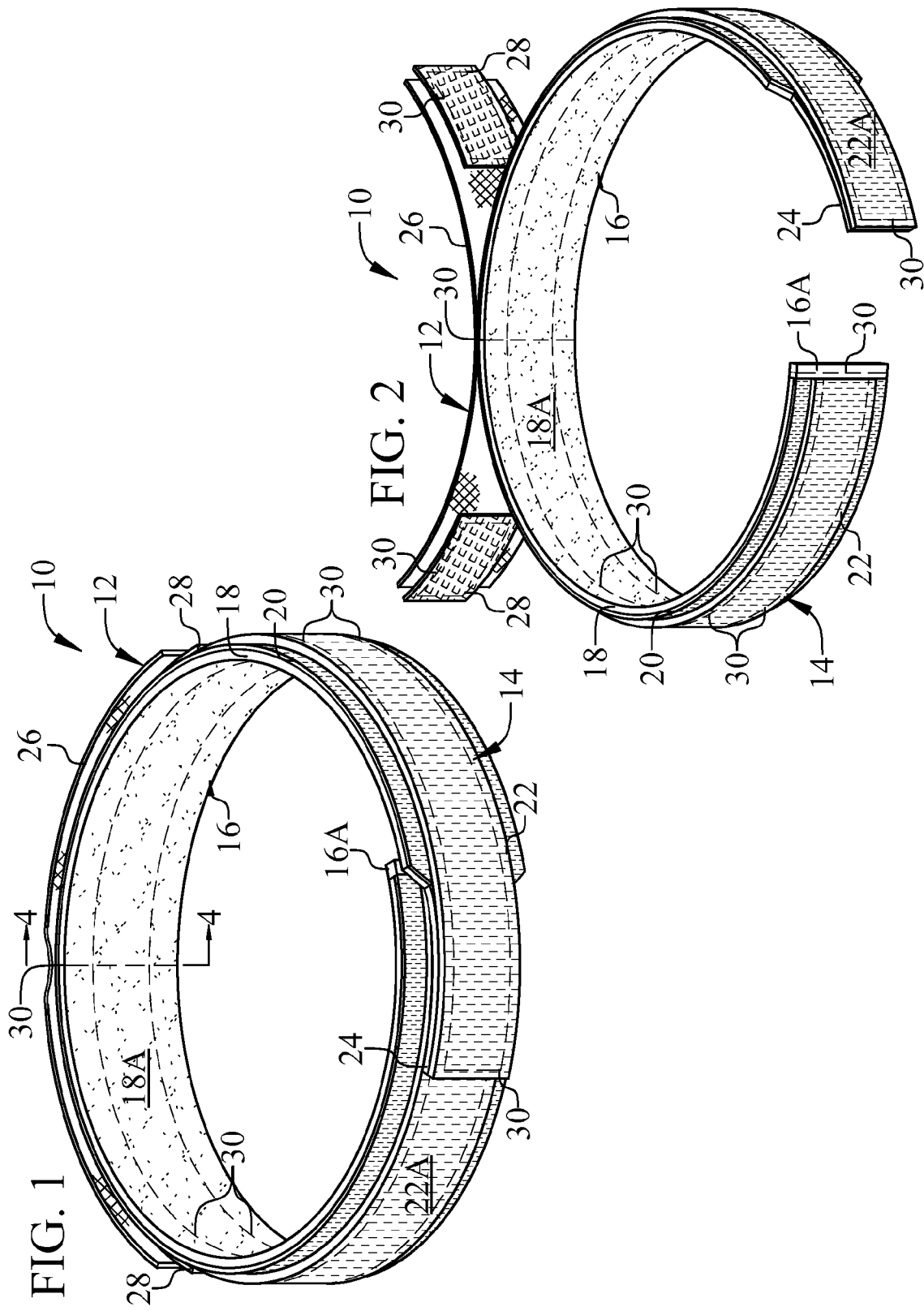

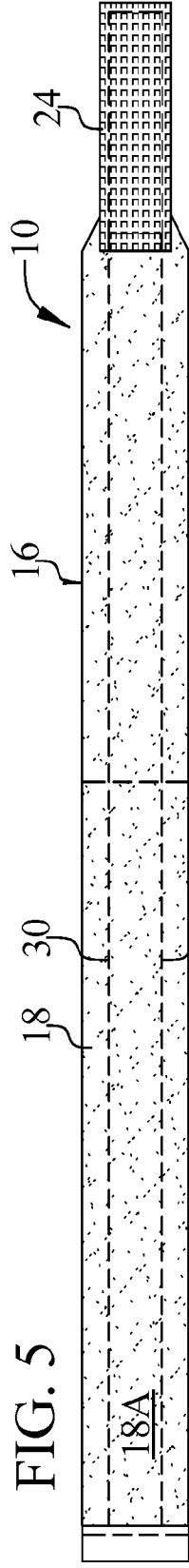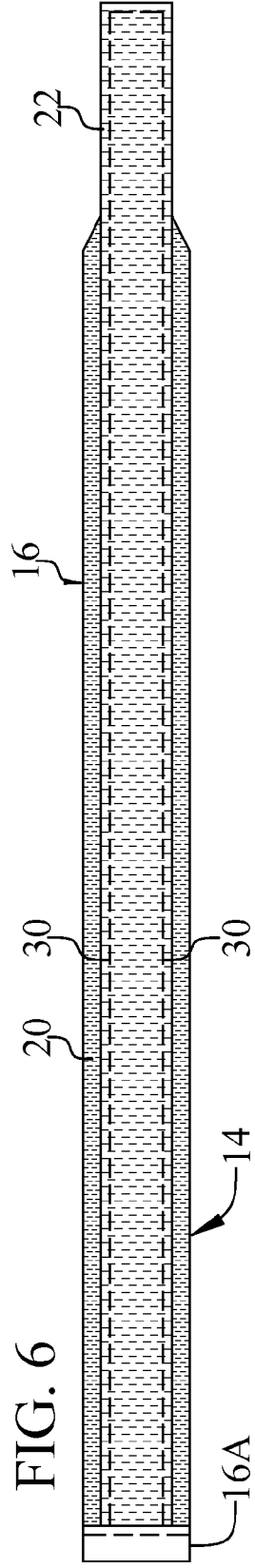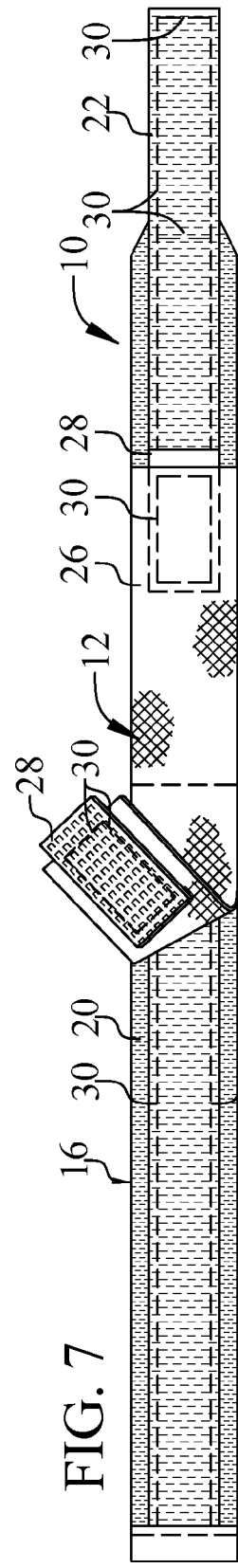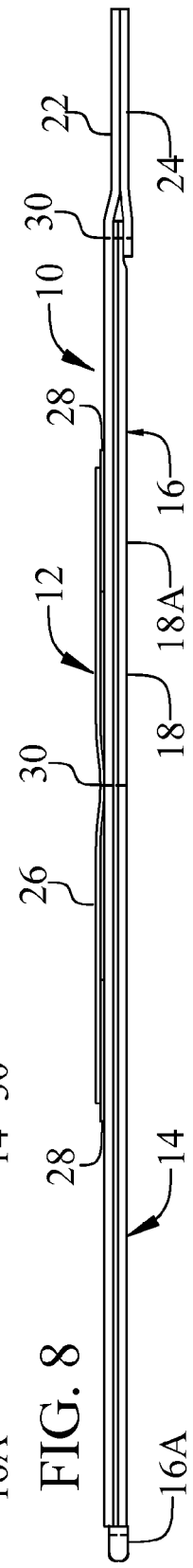

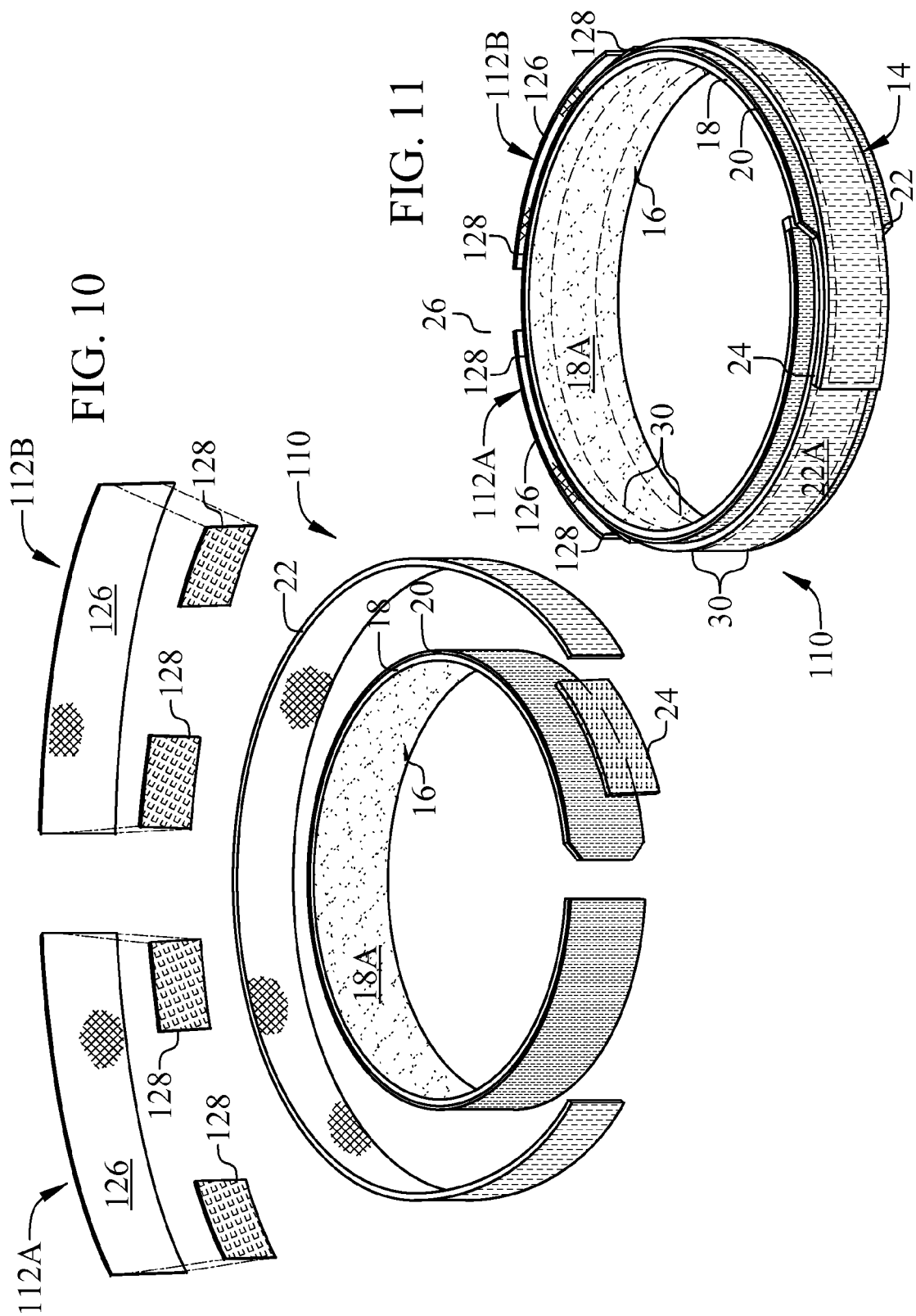

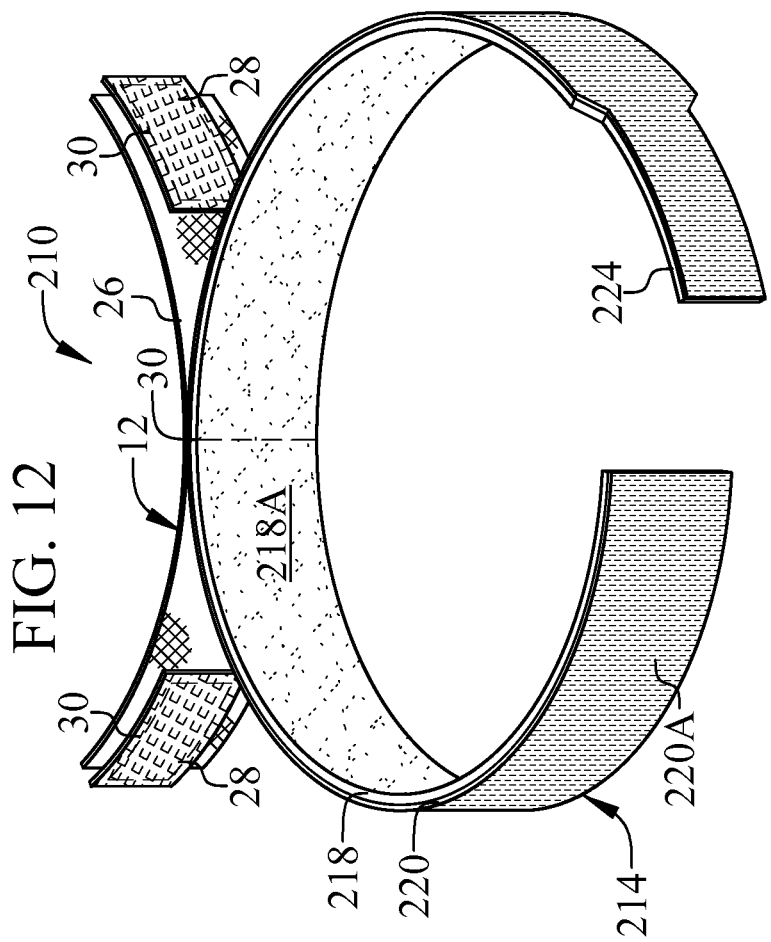

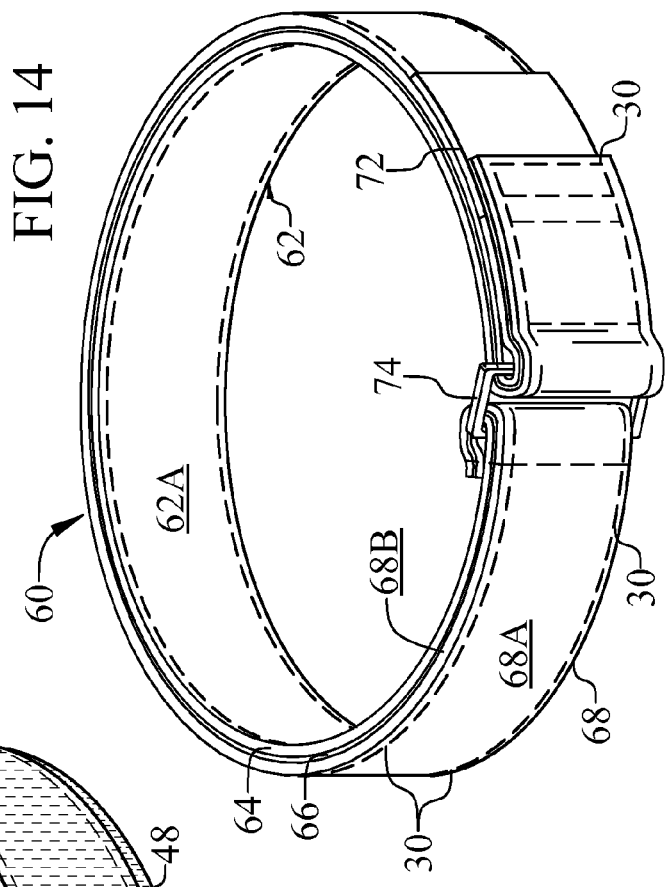
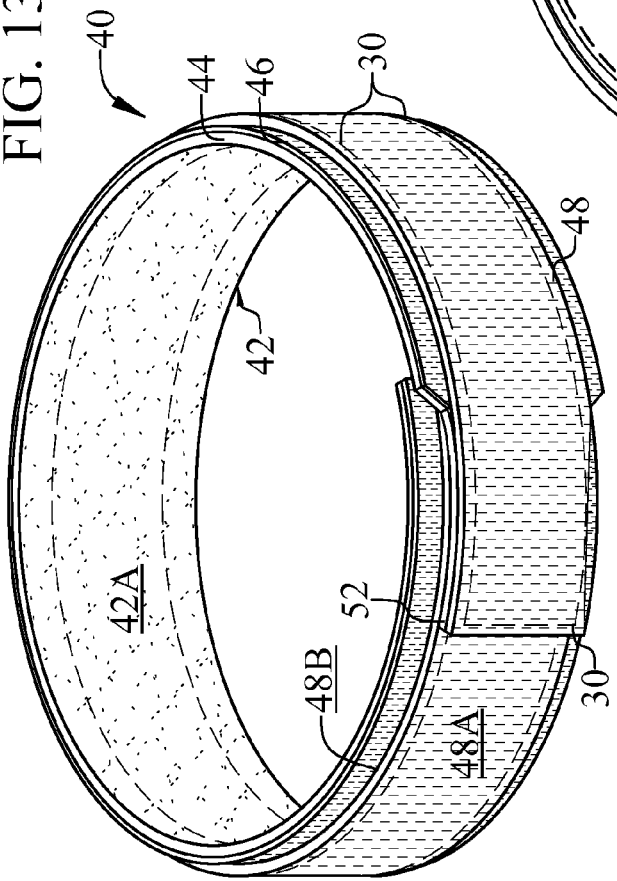

SACROILIAC BELT AND COMPOSITE STRUCTURE

CROSS-REFERENCES TO RELATED APPLICATIONS

This application is a continuation-in-part of, and claims priority to, U.S. patent application Ser. No. 11/278,632, filed Apr. 4, 2006, which application is incorporated herein be reference.

INCORPORATION-BY-REFERENCE OF MATERIAL SUBMITTED ON A COMPACT DISC

Not Applicable.

STATEMENT REGARDING FEDERALLY SPONSORED RESEARCH OR DEVELOPMENT

Not Applicable.

BACKGROUND OF THE INVENTION

1. Field of Invention

The present invention relates to a sacroiliac belt having a lengthwise non-elastic inner belt for snugly encircling the user's hips and a lengthwise elastic outer belt secured between the back and sides of the inner belt to establish elastic compression on the sacroiliac joint. The invention also relates to a lengthwise non-elastic foam-fabric composite structure for use in sacroiliac belts and other non-elastic orthopedic braces and supports for wrapping around a part of the body.

2. Background Art

A sacroiliac belt is worn around the upper hips, to exert a compressive force around the pelvic girdle, and stabilize and reduce strain in the sacroiliac joint. The technical literature provides details on the placement of sacroiliac belts, and medical, physiological, anatomical and other considerations concerning sacroiliac belts. Therefore, although these considerations are discussed briefly as background information concerning the invention, it will be understood that the practitioner will have or readily obtain a more complete understanding of such aspects and considerations concerning sacroiliac belts from the literature.

One type of sacroiliac belt disclosed in the art includes an elastic inner part that wraps around the user's hips and a non-elastic outer part that encircles the inner part to establish an overall non-elastic sacroiliac belt. Brunswick, U.S. Pat. No. 4,572,167 discloses a sacroiliac belt of this type, with elastic panels and a non-elastic cinch strap encircling the panels. Another sacroiliac belt of this type includes elastic Neoprene to wrap around the user's hips and non-elastic Nylon to wrap around the Neoprene. This sacroiliac belt is not recommended for wearing directly against the skin because the closed-cell structure of Neoprene causes heat build-up which can lead to skin irritation. The overall non-elastic nature of such sacroiliac belts is also not preferred by many practitioners because the outer encircling part typically includes a cinchable fastener arrangement, such as a buckle or cinch, that allows a person additional leverage so that it is possible to pull the sacroiliac belt tighter than it should be. As a result, the overall non-elastic sacroiliac belt of this type can reduce available motion in the sacroiliac joint below its normal range of motion. With reduced motion, the inflow of nutrients and oxygen is reduced and the outflow of cellular waste products is reduced. These waste products are acidic, which lowers the pH within the joint. The body then shunts in calcium to neutralize the acid and arthrosis can develop. Buckles and other fastener arrangements used in such belts can also pinch and be otherwise inconvenient or irritating to the user.

Variations on the overall non-elastic sacroiliac belt with an encircling outer belt are also known in the art. For example, Hyman et al., U.S. Pat. No. 4,576,154 discloses a sacroiliac belt with an inner non-elastic woven belt and small cinch straps securable between the ends of the inner belt. Tyo, U.S. Pat. No. 4,696,291 provides a sacroiliac belt with string lacing to secure rigid plastic support members in position. Sacroiliac belts of this type can also be overtightened by the user, and providing optimum support for pelvic girdle considerations that vary from one individual to another in belts using non-flexible elements (such as in Tyo) presents additional difficulties.

Another type of prior sacroiliac belt is generally elastic, which allows good compression of the sacroiliac joint. The elastic sacroiliac belt will not typically compress too much, to the point of limiting motion of the sacroiliac joint below normal. However, an overall elastic sacroiliac belt gives a false sense of security to the user because the actions that open the sacroiliac joint, i.e., bending, lifting, and twisting, can force the joint open beyond its normal range of motion even with the sacroiliac belt in place. In other words, sacroiliac elastic belts do not create a stop point at the end of the normal range of motion of the sacroiliac joint. As ligaments are essentially non-elastic, movement of the sacroiliac joint beyond its normal range will stress the ligaments and potentially re-injure the joint.

Another sacroiliac belt includes an inner belt of non-elastic woven cotton and an outer elastic belt. The inner belt is secured around the user's hips with a hook and loop fastener or other non-cinchable fastener to establish a non-elastic belt that mimics the function of the sacroiliac ligaments in the sense that non-elastic belt allows the sacroiliac joint to open to the end of its normal range of motion and stop further opening of the joint. The outer belt is elastically secured between the back and sides of the inner belt, partially encircling inner belt, to provide the user with a sense of elasticity within the normal range of motion of the sacroiliac joint. Hand tightening this sacroiliac belt creates sufficient tension to compress the soft tissues so that the sacroiliac belt can create the correct stop point at the normal end of range of sacroiliac joint motion, but this sacroiliac belt cannot be tightened too much as to restrict sacroiliac joint motion below its normal range of motion.

A problem with all prior sacroiliac belts is that there is no convenient or comfortable way to attach it to conventional clothing, and due to the inward curvature of the upper part of the hips, the sacroiliac belt can slide up as the user moves around. It is possible to mechanically secure the sacroiliac belt, such as looping a cord or other material from the sacroiliac belt, under the hips, between the legs, and then back up to the sacroiliac belt on the other side of the body; but such arrangements are uncomfortable and inconvenient for the user. Some sacroiliac belts use side patches of open-weave material with rubberized or soft polyvinyl chloride (PVC) composition coating (such as sold under the trademark "GRIPTEX") on the inside of the belt for the suggested purpose of assisting in holding the belt in position. Such patches rely on development of a tackiness or rubber-type surface friction component for gripping purposes with the belt snug around the user. However, in practice, such patches do not exhibit sufficient gripping to hold the sacroiliac belt in position under many conditions or over many materials of clothing. Coating of the weave material results in a relatively smooth surface characteristic which, although somewhat tacky when dry, becomes slippery when wet. Consequently, such patches contribute very little gripping when the belt is worn directly against the skin due to likely presence of small amounts of sweat. The composition of the coating can also be irritating to some people if the sacroiliac belt is worn against the skin.

Thus, there is a need for a sacroiliac belt that addresses the above-identified disadvantages and drawbacks of prior sacroiliac belts. In particular, there is a need for a sacroiliac belt that provides controlled support with limited elasticity within the normal range of motion of the sacroiliac joint, but that can be worn directly against the skin without causing irritation to the user and that remains in place while the user moves around regardless of whether worn against the skin or over clothing.

SUMMARY OF THE INVENTION

An important objective of the invention is to provide a new and improved sacroiliac belt configured to establish controlled support with limited elasticity, wherein, the sacroiliac belt comprises a non-elastic inner belt to be wrapped snugly around the user's hips and an elastic outer belt to be secured between the back and sides of the inner belt.

A detailed objective of the invention is to achieve the foregoing in a sacroiliac belt having an inner belt comprising a bi-laminate with an inside layer of open cell elastomeric rubber or plastic composition foam having an open cell frictional surface characteristic for gripping engagement encircling the user's hips, and loop material (of a hook and loop fastener arrangement) along the outside length for securing the inner belt around the user's hips and securing the outer belt to the inner belt utilizing hook tabs (of a hook and loop fastener arrangement) secured to applicable ends thereof.

A more detailed objective of the invention is to achieve the foregoing in a sacroiliac belt having an inner belt comprising an elastic bi-laminate with said layer of foam laminated to elastic fabric, and a non-elastic strip of loop material secured to the fabric side of the bi-laminate along the length thereof.

Another more detailed objective of the invention is to achieve the foregoing in a sacroiliac belt having an inner belt comprising a bi-laminate with said layer of foam laminated to non-elastic fabric, preferably loop-material fabric (i.e., fabric with loops of a hook and loop fastener arrangement).

Another important objective of the invention is to provide a new and improved non-elastic foam-fabric composite comprising an elastic bi-laminate with a layer of open cell elastomeric composition foam having an open cell frictional surface characteristic laminated to elastic fabric, and a non-elastic strip of loop material secured to the fabric side of the bi-laminate along the length thereof.

These and other objectives and advantages of the invention will become more apparent from the following detailed description when taken in conjunction with the accompanying drawings.

A sacroiliac belt in accordance with the invention includes a non-elastic inner belt and an elastic outer belt. The inner belt is sized in length to wrap around the user's hips. The outer belt is sized in length to wrap from the back and engage opposite sides of the inner belt. The preferred sacroiliac belt utilizes hook and loop fasteners in a non-cinchable arrangement (or other non-cinchable fasteners), to secure the inner belt snugly around the user and the outer belt in elastic compression partially encircling the inner belt.

The inner belt includes an inside layer of elastomeric foam and an outside layer or strip of lengthwise non-elastic loop material. The loop material provides the "loop" surface of a hook and loop fastener arrangement. A hook tab, providing the "hook" surface of a hook and loop fastener arrangement, is secured at one end of the inner belt for engaging the loop material proximate the other end of the inner belt when the inner belt is wrapped around the user's hips. Hook tabs are also provided for securing the elastic outer belt to the inner belt.

The foam is an elastomeric composition, open-cell foam. The open-cell nature of the foam results in many tiny, soft "edges" at the boundaries of the open cells that develop a relatively high coefficient of friction, or frictional surface characteristic, that maintains the sacroiliac belt in position when wrapped snugly around the user's hips. Advantageously, this surface frictional component is substantially unaffected by the presence of limited sweat and other moisture as may develop if the belt is worn directly against the skin. The foam is also breathable and preferably hypoallergenic, and provides positive moisture wicking characteristics, to carry moisture away from the skin, so the sacroiliac belt can be worn directly against the skin, if desired, without heat or moisture buildup or causing skin irritation. The open-cell elastomeric composition foam may be made from urethane-based composition, acrylic-based composition, or other rubber or plastic composition meeting the objectives of the invention as described herein.

In one preferred embodiment, the inner belt is a lengthwise non-elastic foam-fabric composite established with an elastic bi-laminate comprising the foam layer coated onto or bonded, adhered or otherwise laminated to stretchable or elasticized fabric. In this embodiment, the inner belt further includes a strip of loop material comprising loops secured to a thin non-elastic nylon or similar backing that is sewn, bonded, adhered or otherwise firmly secured onto the fabric side of the bi-laminate extending along the length thereof. The full-length non-elastic strip of loop material transforms the elastic bi-laminate into the lengthwise non-elastic inner belt of the sacroiliac belt. The inner belt may further include a strip or width of cushion extending over the upper and lower edges of the strip of loop material, to cushion against the edges of the backing strip from digging into the wearer, particularly when the sacroiliac belt is worn directly against the skin. These strips or widths of cushion may be provided by extending the width of the elastic bi-laminate past the edges of the strip of loop material.

In an alternate embodiment, the inner belt is established with a non-elastic bi-laminate comprising the foam layer laminated to lengthwise non-elastic loop fabric that provides the outside loop element of the hook and loop fastener arrangement in the sacroiliac belt.

The invention also contemplates use of the lengthwise non-elastic foam-fabric composite described above in other types of orthopedic braces and supports of the type that include a non-elastic belt, band, body portion or other non-elastic layer for wrapping around a part of the body for compression, protection, support or other orthopedic purposes.

BRIEF DESCRIPTION OF THE DRAWINGS

FIG. 1 is a perspective view of a sacroiliac belt in accordance with the invention, the sacroiliac belt being shown in a closed condition as would be worn by a user; the sacroiliac belt having a non-elastic inner belt and an elastic outer belt, the inner belt comprising an inside foam-fabric bi-laminate secured to an outside strip of loop material.

FIG. 2 is a perspective view of the sacroiliac belt shown in FIG. 1, but showing the inner belt open and the ends of the outer belt detached from the inner belt.

FIG. 5 is a view of the inside of the sacroiliac belt shown in FIG. 1 as laid flat.

FIG. 6 is a view of the outside of the inner belt shown in FIG. 1 as laid flat (i.e., the outside of the sacroiliac belt shown in FIG. 1 as laid flat with the outer belt not shown).

FIG. 7 is a view of the outside of the sacroiliac belt shown in FIG. 1 as laid flat, with one end of the outer belt peeled away from the inner belt and turned up for viewing the inside details thereof.

FIG. 8 is a top view of the sacroiliac belt shown in FIG. 1 as laid flat, the bottom view being a mirror image thereof.

FIG. 10 is an exploded perspective view of an alternate sacroiliac belt in accordance with the invention.

FIG. 11 is a perspective view of the alternate sacroiliac belt shown in FIG. 10.

FIG. 12 is a perspective view of a second alternate sacroiliac belt in accordance with the invention.

FIG. 13 is a perspective view of an orthopedic band utilizing a lengthwise non-elastic foam-fabric composite in accordance with the invention.

FIG. 14 is a perspective view of an alternate orthopedic band utilizing a lengthwise non-elastic foam-fabric composite in accordance with the invention.

Figures 4A, 4B:
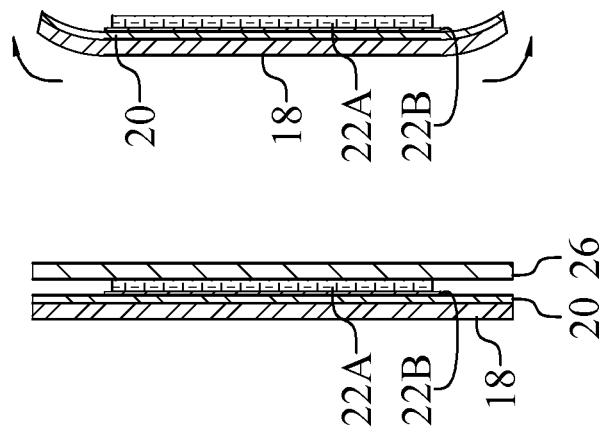
FIG. 4A is a cross-sectional view taken along line 4-4 of FIG. 1.
FIG. 4B is a cross-sectional view similar to FIG. 4A, but with the outer belt not shown, and with the upper and lower widths of the foam-fabric bi-laminate curved over (as may naturally occur when the sacroiliac belt is worn) to establish a lengthwise cushion over and under the upper and lower edges, respectively, of the strip of loop material.
Figure 3:
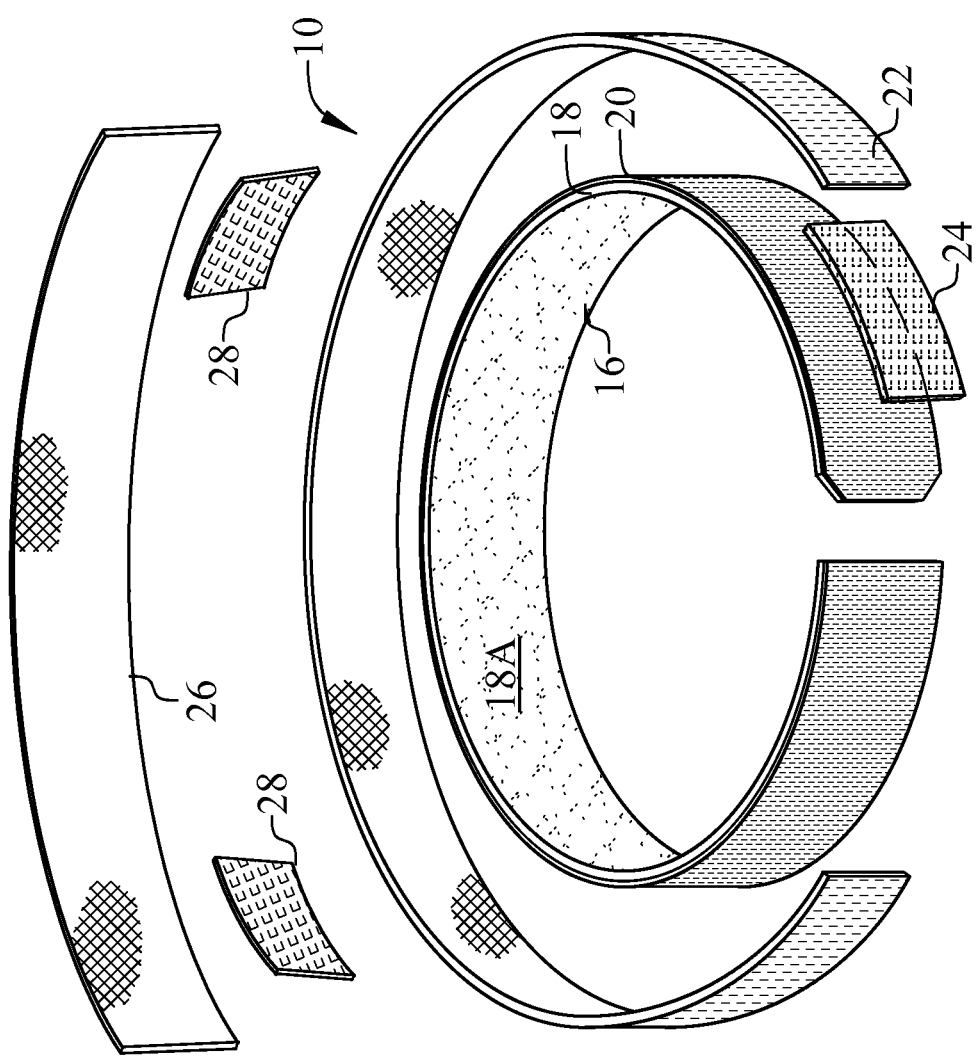
FIG. 3 is an exploded perspective view of the sacroiliac belt shown in FIG. 1.

While the invention is susceptible of various modifications and alternative constructions, certain illustrated embodiments have been shown in the drawings and will be described below in detail. It should be understood, however, that there is no intention to limit the invention to the specific forms disclosed, but on the contrary, the intention is to cover all modifications, alternative constructions, and equivalents falling within the spirit and scope of the invention.

DETAILED DESCRIPTION OF THE INVENTION

Figure 9:
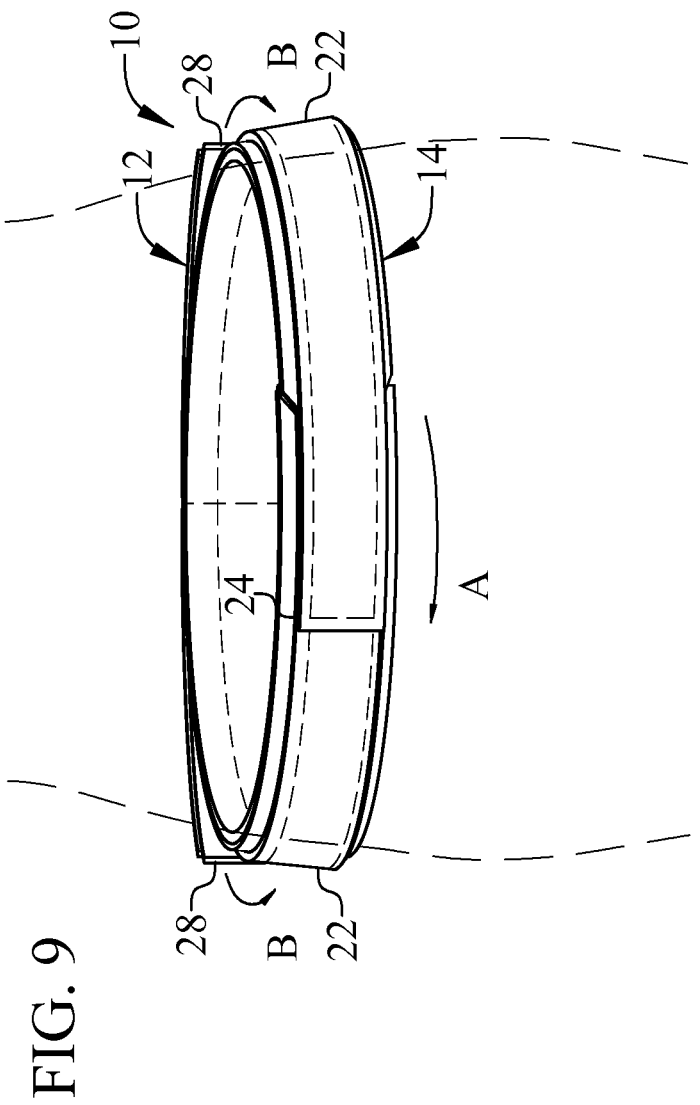
FIG. 9 is perspective view of the sacroiliac belt shown in FIG. 1 as positioned on the hips (shown in dashed lines) of a user.

Referring now to FIGS. 1-9, there is shown a preferred embodiment sacroiliac belt 10 in accordance with the invention. The sacroiliac belt 10 comprises two independently operable belt elements: a lengthwise elastic outer belt 12 and a lengthwise non-elastic inner belt 14. The inner belt 14 is sized in length to wrap around the user's hips (FIG. 9). The outer belt 12 is sized in length to wrap from the back of the user and engage opposite sides of the inner belt. Hook and loop fasteners in non-cinchable arrangements secure the inner and outer belts in position.

The inner belt 14 includes an inside elastic bi-laminate 16 and an outside non-elastic strip 22 of loop material (of hook and loop fastener construction). A hook tab 24 (of hook and loop fastener construction) is secured at one end of the inner belt 14, with the hooks facing inwardly for connecting to the outwardly facing loops of the strip 22 when the inner belt is wrapped around the user or otherwise in a closed condition (FIG. 1). In the embodiment shown, an optional cloth cap 16A is sewn over one end of the bi-laminate and strip of loop material. Stitching is indicated by dashed lines and reference numeral 30.

The elastic bi-laminate 16 is comprised of an elastic foam layer 18 bonded, adhered or otherwise laminated to an elastic fabric 20 that extends the length and width of the foam layer. The foam is an elastomeric rubber or plastic composition, open cell foam such as made from urethane-based, acrylic-based or other suitable polymers. The open-cell nature of the foam establishes a large number of soft tiny edges at the boundaries of the cells, resulting in a relatively high coefficient of friction or frictional surface characteristic on the surface 18A along the inside length of the inner belt 14, thereby resulting in frictional encircling engagement around the user's hips, and maintaining the inner belt in position during normal use. The open-cell foam is also breathable and provides positive moisture wicking to carry moisture away from the skin so that the sacroiliac belt can be comfortably worn against the skin. The elastic fabric is preferably unbroken loop fabric having loop construction of a hook and loop fastener arrangement on its exposed side, but the fabric may be of alternate construction.

The strip 22 of loop material includes an outer layer 22A (FIG. 4A) of loops (of hook and loop fastener construction) on a thin nylon or other non-elastic backing 22B that extends to establish the loop element of a hook and loop fastener along the outside length of the inner belt 14. The non-elastic strip of loop material runs the length of the bi-laminate 16, with the backing 22B sewn, adhered or otherwise secured lengthwise to the exposed fabric side of the bi-laminate, thereby establishing the overall lengthwise non-elastic characteristic of inner belt 14. In this instance, the hook tab 24 is sewn to the inside of the strip 22 at an end that extends past the bi-laminate.

In the preferred embodiment shown, the elastic bi-laminate 16 extends widthwise beyond the backing strip 22B. As shown in FIG. 4B, this additional bi-laminate width is capable of stretching, folding, rolling, etc. over the lengthwise edges of the backing 22B to establish lengthwise cushions over the edges of the loop material backing strip while the sacroiliac belt is worn. The preferred loops 22A in the strip 22 of loop material are substantially larger than the size of loop in the unbroken loop fabric of the bi-laminate for enhanced holding strength while the sacroiliac belt 10 is in position on the user. Advantageously, the additional width of unbroken loop fabric provides additional connection width for the hook tab 24 if not precisely aligned with the strip 22 of loop material.

The outer elastic belt 12 comprises a strip 26 of elastic fabric and a pair of hook tabs 28 at the ends of the elastic strip. The elastic strip is approximately one-half the length of the inner belt 14, and is sewn or otherwise secured (or securable) at the back of the inner belt to establish two outer elastic halves each of which terminate proximate the sides of the inner belt. The hook tabs 28 are sewn or otherwise secured to the ends of the elastic strip, facing inwardly towards the inner belt and the strip 22 of loop material. Alternately, for example, a third hook tab 28 may be sewn to the center of the elastic strip 26 for releasable connection to the strip 22 of loop material at the back of the inner belt.

With this arrangement, the sacroiliac belt 10 is put on by wrapping the non-elastic inner belt 14 snugly around the user's hips, as indicated by arrow "A" in FIG. 9, and securing the hook tab 24 into engagement with the strip 22 of loop material on the other side of the belt. The elastic halves of the outer belt 12 are then drawn firmly from the back around to the sides of the wearer's hips, as indicated by arrows "B" in FIG. 9, until comfortable compression is established in the sacroiliac joint, and secured with the hook tabs 28 engaging the loop material 22 at the sides of the inner belt 14.

Referring to FIGS. 10-11, an alternate embodiment sacroiliac belt 110 in accordance with the invention is shown, wherein the same reference numbers identify identical elements shown in FIGS. 1-9 and described above, and reference numbers for similar elements are incremented by 100. The sacroiliac belt 110 comprises two independently operable belt elements: the non-elastic inner belt 14 described above, and an outer belt comprising two elastic outer-belt segments 112A and 112B. Each outer-belt segment 112A, 112B includes a strip 126 of elastic fabric and a pair of hook tabs 128. Each elastic strip 126 is approximately one-fourth the length of the inner belt 14, with a hook tabs 128 sewn or otherwise secured to each end of the elastic strip positionable facing inwardly towards the inner belt 14 and the strip 22 of loop material. The outer-belt segments 112A, 112B are, together, structurally and operatively similar to outer belt 12 described above. Thus, the sacroiliac belt 110 is put on and worn similar to sacroiliac belt 10 described above, except that the outer-belt segments 112A and 112B are independently securable to the strip of loop material on the outside of the inner belt, for independent connection between the back and sides of the inner belt, or as otherwise desired to draw the inner belt into elastic limited compression around the user's hips.

A second alternate embodiment sacroiliac belt 210, in accordance with the invention, is shown in FIG. 12, wherein the same reference numbers identify identical elements shown in FIGS. 1-9 and described above, and reference numbers for similar elements are incremented by 200. The sacroiliac belt 210 comprises two independently operable belt elements: a non-elastic inner belt 214 sized in length to wrap around the wearer's hips, and the elastic outer belt 12 discussed above. The inner belt 214 includes a non-elastic bi-laminate comprised of an elastic foam layer 218 bonded, adhered or otherwise laminated to non-elastic unbroken loop fabric 220 that extends the length and width of the foam layer, the loop fabric 220A providing the loop element of hook and loop fastener construction along the outside length of the inner belt 214. The foam is elastomeric composition as described above to establish an open cell frictional gripping surface 218A with positive moisture wicking along the inside length of the inner belt 214 for encircling engagement around the user's hips. A hook tab 224 is secured at one end of the inner belt 214 for connecting with the outside loop surface 220A of the bi-laminate when the inner belt is wrapped around the user.

In accordance with another aspect of the invention, the non-elastic foam-fabric composite described above can be used in other types of orthopedic braces and supports that require a non-elastic belt, band, strip, body portion or other non-elastic layer for wrapping around a part of the body, such as, for example, elbow braces and knee braces. Referring to FIG. 13, there is shown an orthopedic band 40 comprising a non-elastic foam-fabric composite with an inside elastic bi-laminate 42 sized in length to wrap around a part of a user's body, and a non-elastic strip 48 of loop material sewn or otherwise secured lengthwise onto the fabric side of the bi-laminate. The elastic bi-laminate is comprised of an elastic foam layer 44 bonded, adhered or otherwise laminated to elastic fabric 46 that extends the length and width of the foam layer. The foam is of open cell elastomeric composition as described above to establish a frictional gripping, breathable inside surface 42A with positive moisture wicking for encircling engagement around the user. The elastic fabric is preferably unbroken loop fabric.

The strip 48 of loop material includes an outer layer 48A of loops on a thin nylon or other non-elastic backing 48B (as shown in detail in FIG. 4A in connection with belt 10) that extends to establish the loop element of a hook and loop fastener along the outside length of the bi-laminate 42. The non-elastic strip of loop material runs the length of the bi-laminate, with the backing 48B sewn, adhered or otherwise secured lengthwise to the exposed fabric side of the bi-laminate, thereby establishing the overall lengthwise non-elastic characteristic of band 40. The bi-laminate 42 shown is wider than the strip 48 of loop material to establish a cushion over the edges thereof. A hook tab 52 is secured at one end of the strip of loop material, facing oppositely of the exposed loop fabric 48A. With this arrangement, the composite non-elastic band 40 is used by wrapping snugly around a part of the user's body, and securing the hook tab 52 at one end of band into engagement with the loop material 48A on the opposite end of the band.

Alternately, for example, a non-elastic foam-fabric composite in accordance with the invention may be used in an orthopedic band 60 such as shown in FIG. 14 with a cinchable fastener arrangement. The band 60 comprises an inside elastic bi-laminate 62 sized in length to wrap around a part of a user's body, and a non-elastic strip 68 of loop material sewn or otherwise secured lengthwise onto the fabric side of the bi-laminate. The elastic bi-laminate is comprised of an elastic foam layer 64 bonded, adhered or otherwise laminated to elastic fabric 66 that extends the length and width of the foam layer. The foam is of elastomeric composition as described above to establish a breathable, open cell frictional inside gripping surface 62A with positive moisture wicking for encircling engagement around the user. The strip of loop material includes an outer layer 68A of loops on a thin nylon or other non-elastic backing 68B (as shown in detail in FIG. 4A in connection with belt 10) that extends to establish the loop element of a hook and loop fastener along the outside length of the bi-laminate. The non-elastic strip of loop material runs the length of the bi-laminate, with the backing 48B sewn, adhered or otherwise secured lengthwise to the exposed fabric side of the bi-laminate, thereby establishing the overall lengthwise non-elastic characteristic of band 60. In this embodiment, a hook tab 72 is secured at one end of the band facing the same direction as the loop material, and a ring 74 is secured to the opposite end of the band such that the hook tab and a length of the band can slip through the ring and fold back for connecting the hook tab to the loop material proximate that end of the band as shown in FIG. 14.

From the foregoing, it will be apparent that the present invention brings to the art a unique sacroiliac belt and orthopedic non-elastic foam-fabric composite with a bi-laminate having a elastomeric composition foam with open-cell frictional gripping and positive moisture wicking characteristic that can be placed directly on the skin, if desired, and that remains in place while the user moves around.

The invention claimed is:

1. A non-elastic foam-fabric composite band for use in orthopedic braces and supports comprising:

a) a first layer of an elastic bi-laminate comprising an inside elastic foam layer and an elastic fabric layer, the elastic foam layer extending the length and width of the elastic fabric layer and being laminated thereto, the elastic foam layer having an open-cell frictional gripping surface and positive moisture wicking characteristic;

b) a second layer of unbroken loop material extending the length of the elastic bi-laminate, the second layer of unbroken loop material comprising a non-elastic strip having an outer layer of loops on a non-elastic backing layer, the non-elastic backing layer being secured against the elastic fabric layer of the elastic bi-laminate opposite the elastic foam layer along the length thereof, the elastic foam layer and elastic fabric layer being rendered lengthwise non-stretchable along their entire secured lengths by the second layer of unbroken loop material secured thereto; and c) a hook and loop fastener construction comprising a loop element formed by the second layer of unbroken loop material and a hook tab secured proximate one end of the second layer of unbroken loop material for securing the hook tab to the outer layer of loops.

2. The composite band as defined in claim 1 in which the hook tab is positioned for connecting to the second layer of unbroken loop material in a non-cinchable fastening arrangement.

3. The composite band as defined in claim 1 in which the first layer extends widthwise beyond the second layer of unbroken loop material to establish an elastic lengthwise cushion over the edges of the strip of non-stretchable loop material.

4. The composite band as defined in claim 1 further comprising a ring secured proximate the end of the loop material opposite the hook tab, and in which the hook tab is sized to be slipped through the ring and secured to the loop material.

5. A method for manufacturing a non-elastic foam-fabric composite band for use in orthopedic braces and supports, the composite band comprising a first layer of an elastic bi-laminate and a second layer of non-elastic strip of unbroken loop material, the second layer of non-elastic strip of unbroken loop material comprising a non-elastic strip having an outer layer of loops on a backing layer, the second layer of non-elastic strip of unbroken loop material secured to the first layer, the method comprising:

a) providing
 i) an elastic bi-laminate comprising:
  a) an elastic foam layer having an open-cell frictional gripping surface and positive moisture wicking characteristic, and
  b) an elastic fabric layer laminated to and extending the length and width of the elastic foam layer;
 ii) a layer of non-elastic strip of unbroken loop material comprising a non-elastic strip having an outer layer of loops on a non-elastic backing layer; and
 iii) a hook tab; and
b) securing:
 i) the layer of non-elastic strip of unbroken loop material to the elastic fabric layer of the bi-laminate along the length thereof with the non-elastic backing layer against the elastic fabric layer, thereby rendering the bi-laminate lengthwise non-elastic along its length by the layer of non-elastic strip of unbroken loop material secured thereto, and
 ii) the hook tab proximate one end of the layer of non-elastic strip of unbroken loop material.

6. The method as defined in claim 5 further comprising providing and securing a ring proximate an end of the layer of non-elastic strip of unbroken loop material opposite the end proximate the hook tab, the hook tab being sized to be slipped through the ring and secured to the strip of loop material.

7. The method as defined in claim 5 in which the hook tab is positioned for connecting to the non-elastic strip of unbroken loop material in a non-cinchable fastening arrangement.

8. A sacroiliac belt comprising:
a) a non-elastic inner belt configured for encircling placement around a user's hips, the inner belt having
 i) an inside layer of an elastic bi-laminate comprising an elastic foam layer and an elastic fabric layer, the elastic foam layer extending the length and width of the elastic fabric layer and being laminated to the elastic foam layer, the elastic foam layer having an open-cell frictional gripping surface and positive moisture wicking characteristic, the elastic foam layer extending lengthwise for encircling engagement around a user's hips;
 ii) an outer layer of unbroken loop material of hook and loop fastener construction extending in secured relation the length of the inside layer of the elastic bi-laminate for encircling placement around the user's hips, the outer layer of unbroken loop material comprising a non-elastic strip having an outer layer of loops on a non-elastic backing layer, the non-elastic backing layer being secured against the elastic fabric layer of the elastic bi-laminate opposite the elastic foam layer along the length of the elastic bi-laminate, the elastic foam layer and elastic fabric layer being rendered lengthwise non-stretchable along their entire secured lengths by the outer layer of unbroken loop material secured thereto; and
 iii) a hook tab at one end thereof in fastening engageable relation with the unbroken loop material with the inner belt encircling the user's hips; and
b) an elastic outer belt sized to extend forwardly from the back of the inner belt to the sides thereof, the outer belt having hook tabs for connecting to the outer layer of loops of the inner belt.

9. The sacroiliac belt as defined in claim 8 wherein the elastic bi-laminate extends widthwise beyond the edges of the outer layer of unbroken loop material to establish an elastic lengthwise cushion over the edges of the outer layer of loop material.

10. The sacroiliac belt as defined in claim 8 in which the hook tabs of the elastic outer belt are positioned for connecting to the loops of the outer layer of unbroken loop material in a non-cinchable fastening arrangement.

11. The sacroiliac belt as defined in claim 8 further comprising a lengthwise elastic cushion extending widthwise beyond the edges of the strip of loop material.

12. The sacroiliac belt as defined in claim 11 in which the elastic bi-laminate extends widthwise beyond the strip of loop material to establish said lengthwise cushion.

13. The sacroiliac belt as defined in claim 8 in which the outer belt comprises an elastic strip extending from side to side around the back of the inner belt.

14. The sacroiliac belt as defined in claim 8 in which the outer belt comprises a pair of elastic strips each independently connectable to the inner belt and sized to extend from proximate the back of the inner belt to respective sides of the inner belt.

* * * * *